United States Patent [19]
Vedage et al.

[11] Patent Number: 5,886,227
[45] Date of Patent: Mar. 23, 1999

[54] PROCESS FOR HYDROGENATION OF CYANOPROPIONALDEHYDE-CONTAINING CYANOPROPIONADELHYDE ACETALS

[75] Inventors: Gamini Ananda Vedage, Bethlehem; Kathryn Sue Hayes, Norristown, both of Pa.

[73] Assignee: Air Products and Chemicals, Inc., Allentown, Pa.

[21] Appl. No.: 958,894

[22] Filed: Oct. 28, 1997

[51] Int. Cl.⁶ .................................................. C07C 209/48

[52] U.S. Cl. .......................... 564/490; 564/491; 564/473; 564/504

[58] Field of Search .................................. 564/490, 491, 564/493, 504

[56] References Cited

U.S. PATENT DOCUMENTS

| | | | |
|---|---|---|---|
| 4,885,391 | 12/1989 | Herkes | 564/491 |
| 5,741,930 | 4/1998 | Hearn et al. | 564/490 |

*Primary Examiner*—Ba K. Trinh
*Attorney, Agent, or Firm*—Russell L. Brewer

[57] ABSTRACT

Disclosed is an improved process for the catalytic hydrogenation of cyanopropionaldehyde alkyl acetals (CPAA) to form the aminobutyraldehyde alkyl acetals. The basic process comprises hydrogenating the cyanopropionaldehyde alkyl acetals by contacting said cyanopropionaldehyde alkyl acetals with hydrogen in the presence of a nickel or cobalt catalyst under conditions for reducing the nitrile group to the primary amine. The improvement resides in effecting the hydrogenation of a cyanopropionitrile dialkyl acetal feedstock containing contaminating levels of cyanopropionaldehyde in the presence of a secondary alkanol or water.

14 Claims, No Drawings

PROCESS FOR HYDROGENATION OF CYANOPROPIONALDEHYDE-CONTAINING CYANOPROPIONADELHYDE ACETALS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Aminobutyraldehyde dimethyl acetal (ABAA) is an amine which can be incorporated into polymers to provide crosslinkable functionality useful in coatings formulations. The advantage of coatings technology based on ABAA and other aminoalkylaldehyde alkyl acetals is that it can avoid the use of formaldehyde-based crosslinkers. Legislation requiring reduction of such formaldehyde emissions has become increasingly stringent and coatings formulators and resin manufacturers have become receptive to alternative, more environmentally benign technologies.

ABAA, and other aminopropionaldehyde acetals are typically produced by hydrogenation of the corresponding nitrile, a material in turn produced by catalytic hydroformylation of acrylonitrile in an alcohol solvent. The initially-formed cyanopropionaldehyde is converted under the reaction conditions to the cyanopropionaldehyde acetal by reaction with an alcohol. The reaction product is distilled to remove impurities and then hydrogenated.

The following patents are relevant to the hydrogenation of nitriles:

U.S. Pat. No. 2,449,036 discloses the manufacture of primary amines by the catalytic liquid phase hydrogenation of the corresponding nitrites. In an effort to avoid the formation of secondary and tertiary amines, hydrogenation of nitrites has been carried out in the presence of ammonia or in the presence of substances capable of liberating ammonia. One of the problems was that the addition of ammonia decreased the partial pressure of hydrogen in the reactor which lead to lower rates of reaction than in hydrogenation reactions performed in the absence of ammonia. Cobalt catalysts in combination with an alkali metal hydroxide, e.g., sodium, potassium or lithium hydroxide, or quaternary ammonium bases were found to result in high yields of a primary amine without the concomitant problems associated with the use of ammonia.

U.S. Pat. No. 3,427,356 discloses the preparation of 1,3-propylenediamines by hydrogenating β-aminopropionitriles in the presence of ammonia at temperatures below 200° C., the catalyst for such hydrogenation being cobalt or nickel. The patentees point out that a small amount of a manganese compound dissolved in the hydrogenation mixture enhances the activity of the catalyst with little decomposition of the catalyst or deposition of the polymers thereon.

U.S. Pat. No. 3,896,173 discloses a two stage catalytic hydrogenation of unsaturated dinitriles using ruthenium or nickel as the catalyst. In the process, ammonia is used in the first stage catalytic hydrogenation wherein the nitrile is reduced to the amine. This hydrogenation is followed by a second stage hydrogenation where the ethylenic unsaturation is hydrogenated. Conventional hydrogenation catalysts are deemed suitable for the two stage hydrogenation and these include ruthenium, Raney nickel, and the like.

U.S. Pat. No. 4,375,003 discloses an improved process for preparing primary amines from an aliphatic nitrile and hydrogen. Raney cobalt is used as the catalyst. To avoid the use of ammonia and other bases in an effort to produce primary amines in high yield, a small amount of alkali metal hydroxide is added. The catalyst employed is a Raney cobalt catalyst incorporating from 2–35 weight percent aluminum with a cobalt aluminum alloy being contacted with an aqueous medium containing dissolved alkali metal hydroxide.

European 0 316 761 discloses a process for producing N,N-dimethyldiamino-propane by the catalytic hydrogenation of N,N-dimethylaminopropionitrile in the presence of ammonia and one or more alkaline earth oxides. Raney cobalt is the preferred catalyst.

BRIEF SUMMARY OF THE INVENTION

The present invention pertains to an improved process for the catalytic hydrogenation of cyanopropionaldehyde alkyl acetals (CPAA) to form aminobutyraldehyde alkyl acetals. The basic process comprises hydrogenating the cyanopropionaldehyde alkyl acetal by contacting said cyanopropionaldehyde alkyl acetal with hydrogen in the presence of a nickel or cobalt catalyst under conditions for reducing the nitrile group to the primary amine. The improvement resides in effecting the hydrogenation of a cyanopropionitrile dialkyl acetal feedstock containing contaminating levels of cyanopropionaldehyde or the alkyl ester of cyanopropionic acid in the presence of an additive selected from the group insisting of an alkanol, preferably a secondary alcohol or water.

The presence of an alcohol such as a secondary alcohol or water is effective for imparting the following advantages to the hydrogenation process:

- it has an ability to overcome the difficulties associated with producing a highly purified cyanoalkylaldehyde alkyl acetal feedstock prior to hydrogenation;
- it has an ability to employ a feedstock containing contaminants found to be hydrogenation catalyst poisons;
- it has an ability to dramatically reduce the reaction time associated with hydrogenation; and,
- it has an ability to produce the desired primary amine products in high yield and selectivity.

BRIEF DESCRIPTION OF THE SEVERAL VIEWS OF THE DRAWINGS

Not applicable.

DETAILED DESCRIPTION OF THE INVENTION

This process is useful for the hydrogenation of cyanoalkylaldehyde acetal feeds and particularly cyanopropionitrile dialkyl acetal which contains cyanopropionaldehyde as a reaction contaminant. The reaction chemistry is as follows:

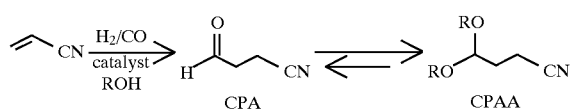

-continued

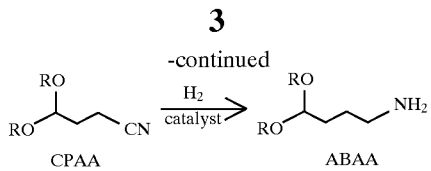

In the above reaction, R is aliphatic, typically alkyl and more particularly an alkyl radical having from 1–8 carbon atoms. It can also be cycloalkyl or aryl and R may be the same or different. Preferably, R is methyl or ethyl. The R group may be the residue of a polyfunctional alcohol which couples to another cyanopropionaldehyde, $C_{1-8}$ alkanols, $C_{1-8}$ alkoxyalkanols, $C_{2-8}$ glycols and polyols, and aryl alcohols. A representative example is as follows:

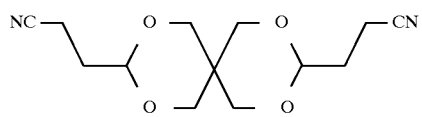

As is known, the acetal is formed by reacting the cyanopropionaldehyde with an alcohol. This reaction typically is done in situ although the reaction may be carried out subsequent to the aldehyde formation. Classes of alcohols suited for forming the acetal are $C_{1-8}$ alkanols, $C_{1-8}$ alkoxyalkanols, $C_{2-8}$ glycols and polyols, and aryl alcohols. Examples of alcohols include methanol, ethanol, 1-propanol, 2-propanol, 1-butanol, 2-butanol, and 2-methyl-2-propanol and so on, ethylene glycol, 1,2-propane diol, 1,3-propane diol, 2-methyl-1,3-propanediol, butylene glycol, methoxypropanol, ethoxyethanol, cyclohexanol, sorbitol, glycerol, pentaerythritol, phenol and benzyl alcohol. Acetals derived from hydroxyl-containing polymers such as polyvinyl alcohol, polyether polyols, and polyester polyols as also applicable for the formation of the acetal. The condensation product derived by the reaction of cyanopropionaldehyde with tetrols can also be employed.

The acetal formation is an equilibrium-controlled process. In the past it has been necessary to rigorously purify the reaction product to remove impurities otherwise hydrogenation was ineffective. It has been found that the presence of only a few tenths of a percent or so of cyanopropionaldehyde or the alkyl ester of cyanopropionic acid in the reaction product can completely inhibit the hydrogenation of the cyanopropionaldehyde alkyl acetals. Even trace quantities of these contaminants can result in an extensive induction period. Because rigorous fractional distillation had been required this process step diminished the efficiency and adversely effected the economics associated with the hydrogenation of cyanopropionitrile dialkyl acetals.

It has been found that one can overcome the problems associated with rigorous distillation of the cyanopropionitrile dialkyl acetals and effect the hydrogenation of relatively crude streams of cyanopropionaldehyde alkyl acetals in the presence of alkanols, preferably secondary alkanols or water. Examples of alkanols suited for the hydrogenation medium include $C_{1-8}$ alkanols such as methanol, ethanol, butanol and the like. Preferably, secondary $C_{3-6}$ alkanols are employed, and these include isopropanol, 2-butanol, 2-pentanol and the like.

The amount of alcohol or water added must be sufficient to substantially consume any cyanopropionaldehyde or alkyl ester of cyanopropionic acid present in the reaction mixture. That is, at least approximately one molar equivalent of secondary alcohol or water based on aldehyde or alkyl ester present in the crude stream of cyanopropionaldehyde alkyl acetal. This translates into levels of about 5 to 75% by weight of alkanol or water based upon the crude feed of cyanopropionaldehyde to be hydrogenated. Somewhat less alkanol or water may be utilized in certain cases, but much less than one equivalent or 5% alkanol or water is unlikely to allow the facile hydrogenation. Further, there appears to be little downside to using larger quantities of alkanol or water except that associated with reactor productivity. Typically, from 10 to 50% by weight alkanol or water, based upon cyanopropionaldehyde feed including trace contaminants, is employed.

Alkali metal hydroxides often are incorporated into the hydrogenation medium in an amount from about 0.1 to 1% based upon the weight of the cyanoalkylaldehyde alkyl acetal feedstock. Too little alkali metal hydroxide can adversely affect the selectivity to the desired aminobutyraldehyde dialkyl acetal and lead to larger amounts of secondary amine byproducts. Too much alkali metal hydroxide can diminish the activity of the catalyst and lead to long reaction times. Alkali metal hydroxides include sodium, potassium and lithium hydroxide. Although they have been added as aqueous dispersions, insufficient water is added with these catalysts to mitigate against the adverse effects of cyanopropionaldehyde or the alkyl esters or cyanopropionic acid.

The catalysts employed in the hydrogenation reaction include the conventional nickel and cobalt hydrogenation catalysts as represented in the prior art cited in the background of the invention. Such descriptions are incorporated by reference. Examples include Raney nickel and Raney cobalt. Also, supported nickel and cobalt catalysts may be employed, the supports generally comprising alumina. Other components such as promoters may be incorporated into the catalyst, e.g., manganese.

The reaction should be run at a temperature sufficient to provide a convenient reaction rate, but low enough to prevent thermal decomposition of the reagents, products, or catalyst. Temperatures from about 40° C. to about 150° C. may be employed, with temperatures from 60° to 120° C. being preferred. Below these temperatures, the rate of reaction is inconveniently low, whereas above these temperatures, decomposition of the product begins to occur.

The reaction should be run at a hydrogen pressure sufficient to induce reaction. Pressures from about 100 psig to about 5000 psig are suitable, preferably about 100–800 psig. Pressures much lower than 100 psig would probably provide an inconveniently low reaction rate. Pressures above 5000 psig would work, but it is not anticipated that these high pressures would provide significant advantage and in all likelihood increase the cost of the capital required to practice the invention.

The process may be practiced in the presence of inert solvents such as ethers, esters, and so on. Practicing in the presence of a solvent may provide processing or other benefits, but that may decrease reactor productivity.

Although not intending to be bound by theory, the addition of isopropanol or water to overcome the effect of catalyst poisoning by cyanopropionaldehyde and/or the alkyl esters of cyanopropionic acid prevents these molecules from undergoing decarbonylation. These carbonyls are produced on the active surface of the catalyst and cause deactivation of the hydrogenation catalyst.

The following examples are provided to illustrate various embodiments of the invention and comparisons thereto and are not intended to restrict the scope thereof.

COMPARATIVE EXAMPLE 1

Hydrogenation of Cyanopropionaldehyde Dimethyl Acetal Free of Cyanopropionaldehyde Using Nickel Catalyst A 1 L autoclave was charged with A4000 chrome-promoted sponge nickel catalyst (marketed by Activated Metals and Chemicals, 4.8 g) in 5 g of water, and cyanopropionaldehyde dimethyl acetal, 625 g. GC analysis of the cyanopropionaldehyde dimethyl acetal showed that it was free of cyanopropionaldehyde.

A solution of $LiOH.H_2O$ (2.1 g) in $H_2O$ (10 mL) was added. Then, the reactor was sealed, purged free of air and the pressure checked with nitrogen. Hydrogen was introduced and the hydrogen pressure adjusted to ca. 500 psig; the reaction mixture was heated to 90° C. When the temperature had equilibrated, the pressure was increased to 750 psig, and maintained by means of a regulated ballast. After about 14 h, the theoretical amount of hydrogen had been consumed and the hydrogen uptake was complete. The product was removed from the reaction vessel and analyzed by GC. Aminobutyraldehyde dimethyl acetal had been formed in 92% yield (molar basis).

Most likely, the level of water was insufficient for reducing the reaction time as is evidenced by other examples.

COMPARATIVE EXAMPLES 2

Hydrogenation of Cyanopropionaldehyde Dimethyl Acetal in the Presence of Cyanopropionaldehyde Using Nickel Catalyst A cyanopropionaldehyde dimethyl acetal feed was analyzed by GC and found to contain 1.9% cyanopropionaldehyde. Hydrogenation of this material was attempted using the procedure of Comparative Example 1. After 16 h at 90° C. and 750 psig, less than 2% of the theoretical quantity of hydrogen had been consumed. GC analysis of the dark brown product showed that it contained only 1.7% aminobutyraldehyde dimethyl acetal, and 94.9% of the material was comprised of unreacted cyanopropionaldehyde dimethyl acetal.

These results show the severe and adverse impact of the presence of contaminant cyanopropionaldehyde on the hydrogenation of cyanopropionaldehyde dimethyl acetal. In Example 1, the yield with a contaminant-free feed was approximately 92% while in this example there was essentially no reaction and almost all of the starting cyanopropionitrile dialkyl acetal remained unconverted.

COMPARATIVE EXAMPLE 3

Hydrogenation of Cyanopropionaldehyde Diethyl Acetal Containing Cyanopropionaldehyde and Cyanopropionaldehyde Diethyl Acetal Using a Cobalt Catalyst 350 g of Cyanopropionaldehyde Diethyl Acetal (CPAA-diethyl) containing 0.2% cyanopropionaldehyde and 0.5% cyanopropionaldehyde diethyl acetal was loaded into a 1 liter autoclave reactor and to that we added 5.7 g of Raney Cobalt marketed by Grace under the designation 2724. The reactor was first purged with several nitrogen pressure vent cycles followed by three pressure vent cycles with hydrogen. The reactor was then pressured to 500 psi with $H_2$ and heated to 100° C. When the reactor reached 100° C. the reactor was pressured to 850 psi. After 600 min. at 850 psi only 4% of the theoretical hydrogen was consumed.

As in Example 2, the contaminants in the feed were detrimental to the effectiveness of cobalt in the hydrogenation of cyanopropionaldehyde.

COMPARATIVE EXAMPLE 4

Hydrogenation of Cyanopropionaldehyde Diethyl Acetal to Aminobutyraldehyde Diethyl Acetal in Presence of DMAPA This experiment was carried out in a 300 cc autoclave reactor. To the 300 cc reactor, was added 80 g of CPAA (same feed as Example 3) 1.35 g of Grace Raney Co 2724 and 2.8 g of dimethylaminopropyl amine (DMAPA). The reactor was first purged with several nitrogen pressure vent cycles followed by three pressure vent cycles with hydrogen. The reactor was then pressured to 500 psi with $H_2$ and heated to 100° C. When the reactor reached 100° C. the reactor was pressured to 850 psi. The hydrogenation was completed in 480 min. The product analysis showed 100% conversion with 93.9% selectivity to ABAA.

This example shows that the addition of the amine, DMAPA, countered the poisonous effects of the contaminants. However, the reaction time was lengthy.

EXAMPLE 5

Hydrogenation of Cyanopropionaldehyde Diethyl Acetal to Aminobutyraldehyde Diethyl Acetal Using DMAPA and Isopropanol The procedure of Example 4 was followed by effecting reaction in a 300 cc autoclave reactor. To the 300 cc reactor, was added 40 g of CPAA (same feed as Example 4), 40 g of isopropanol, 1.4 g of DMAPA and 0.85 g of Grace Raney Co 2724 catalyst. The CPAA to cobalt catalyst and DMAPA ratio was kept essentially the same as Examples 3 and 4. The reactor was first purged with several nitrogen pressure vent cycles followed by three pressure vent cycles with hydrogen. The reactor was then pressured to 500 psi with $H_2$ and heated to 95° C. When the reactor reached 95° C. the reactor was pressured to 850 psi. The hydrogenation was completed in 81 min. The product analysis showed 100% conversion with 96.0% selectivity to ABAA.

This example shows a reduction in reaction time from that of Example 4 by incorporating 50% by weight isopropanol to the reaction medium.

EXAMPLE 6

Hydrogenation of Cyanopropionaldehyde Diethyl Acetal to Aminobutyraldehyde Diethyl Acetal Using DMAPA and Water The procedure of Example 5 was essentially repeated in a 300 cc autoclave reactor. To the 300 cc reactor, was added 80 g of CPAA (same feed as above), 10 g of Dl water, 2.8 g of DMAPA and 0.85 g of Grace Raney Co 2724 catalyst. The reactor was first purged with several nitrogen pressure vent cycles followed by three pressure vent cycles with hydrogen. The reactor was then pressured to 500 psi with $H_2$ and heated to 95° C. When the reactor reached 95° C. the reactor was pressured to 850 psi. The hydrogenation was completed in 110 min. The product analysis showed 100% conversion with 95.1% selectivity to ABAA.

Again the reaction time was reduced substantially by the use of ~12% water and the amine, DMAPA.

EXAMPLE 7

Hydrogenation of Cyanopropionaldehyde Diethyl Acetal to Aminobutyraldehyde Diethyl Acetal Using DMAPA and Water The procedure of Example 4 was repeated essentially in a 300 cc autoclave 20 rector. To the 300 cc reactor, was added 65 g of CPAA, 25 g of Dl water, 2.3 g of DMAPA and 1.14 g of Grace Raney Co 2724 catalyst. The reactor was first purged with several nitrogen pressure vent cycles followed by three pressure vent cycles with hydrogen. The reactor was then pressured to 500 psi with $H_2$ and heated to 95° C. When the reactor reached 95° C. the reactor was pressured to 850 psi. The hydrogenation was completed in 17 min. The product analysis showed 100% conversion with 94.3% selectivity to ABAA.

The Example shows the addition of ~38% water and DMAPA based on CPAA feed reduced the reaction time from that of Example 4.

EXAMPLE 8

Hydrogenation of Cyanopropionaldehyde Diethyl Acetal to Aminobutyraldehyde Diethyl Acetal Using Water W/O DMAPA The procedure of Example 5 was essentially repeated by carrying out the reaction in a 300 cc autoclave reactor. To the 300 cc reactor, was added 65 g of CPAA, 25 g of Dl water and 1.14 g of Grace Raney Co 2724 catalyst. No DMAPA was added. The reactor was first purged with several nitrogen pressure vent cycles followed by three pressure vent cycles with hydrogen. The reactor was then pressured to 500 psi with $H_2$ and heated to 95° C. When the reactor reached 95° C. the reactor was pressured to 850 psi. The hydrogenation was completed in 27 min. The product analysis showed 100% conversion with 95.2% selectivity to ABAA.

The example shows that water alone, when present in sufficient amount, is effective in reducing reaction time.

What is claimed is:

1. In a process for the catalytic hydrogenation of a cyanopropionaldehyde alkyl acetal by contacting said cyanopropionaldehyde alkyl acetal with hydrogen in the presence of a nickel or cobalt catalyst under conditions for reducing the nitrile group to a primary amine group, the improvement which resides in effecting the hydrogenation of a cyanopropionaldehyde alkyl acetal feed containing contaminating levels of cyanopropionaldehyde or the cyanoalkyl ester of cyanopropionic acid or both in the presence of an additive selected from the group consisting of an alkanol or water.

2. The process of claim 1 wherein the cyanopropionaldehyde alkyl acetal is represented by the formula:

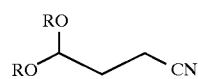

wherein R is aliphatic or aryl and it may be the same or different.

3. The process of claim 2 wherein the R designating the alcohol residue in the cyanopropionaldehyde alkyl acetal is derived from an alcohol selected from the group consisting of $C_{1-8}$ alkanols, $C_{1-8}$ alkoxyalkanols, $C_{2-8}$ glycols and polyols, and aryl alcohols.

4. The process of claim 3 wherein the additive is a secondary alkanol and is incorporated in an amount of from about 5 to 75% by weight of the feed.

5. The process of claim 4 wherein R in said formula is an alkyl radical having from 1–8 carbon atoms.

6. The process of claim 5 wherein the additive incorporated in the hydrogenation process is a $C_{3-6}$ secondary alkanol.

7. The process of claim 6 wherein the additive incorporated in the hydrogenation process is selected from the group consisting of isopropanol, 2-butanol and 2-pentanol.

8. The process of claim 5 wherein the secondary alkanol incorporated in the hydrogenation is selected from the group consisting of isopropanol and isobutanol.

9. The process of claim 3 wherein R is methyl or ethyl.

10. The process of claim 3 wherein the additive is water.

11. The process of claim 10 wherein the water is incorporated in an amount of from about 5 to 75% by weight of the feed.

12. The process of claim 11 wherein R in said formula is an alkyl radical having from 1–8 carbon atoms.

13. The process of claim 12 wherein R is methyl or ethyl.

14. The process of claim 13 wherein the water is incorporated in an amount of from 10 to 50% by weight of the feed.

* * * * *